(12) United States Patent
Sloan et al.

(10) Patent No.: US 9,723,082 B2
(45) Date of Patent: Aug. 1, 2017

(54) MANAGEMENT OF MULTIPLE DEVICES WITHIN AN ANALYTE MONITORING ENVIRONMENT

(71) Applicant: ABBOTT DIABETES CARE INC., Alameda, CA (US)

(72) Inventors: Mark Sloan, Redwood City, CA (US); Nathan Crouther, San Francisco, CA (US); Glenn Berman, Alameda, CA (US); Gil Porat, Mountain View, CA (US); Michael R. Love, Pleasanton, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 31 days.

(21) Appl. No.: 14/717,749

(22) Filed: May 20, 2015

(65) Prior Publication Data

US 2015/0341438 A1 Nov. 26, 2015

Related U.S. Application Data

(60) Provisional application No. 62/001,343, filed on May 21, 2014.

(51) Int. Cl.

| | |
|---|---|
| *H04W 12/00* | (2009.01) |
| *H04L 29/08* | (2006.01) |
| *A61B 5/00* | (2006.01) |
| *G06Q 50/22* | (2012.01) |
| *H04W 4/00* | (2009.01) |
| *H04L 29/06* | (2006.01) |
| *H04W 12/08* | (2009.01) |

(52) U.S. Cl.
CPC ............ *H04L 67/12* (2013.01); *A61B 5/0004* (2013.01); *G06Q 50/22* (2013.01); *H04L 63/0807* (2013.01); *H04W 4/008* (2013.01); *H04W 12/08* (2013.01); *A61B 5/7495* (2013.01)

(58) Field of Classification Search
CPC ...................................................... H04W 4/008
USPC ..................................... 455/41.1, 41.2, 41.3
See application file for complete search history.

(56) References Cited

U.S. PATENT DOCUMENTS

| | | | |
|---|---|---|---|
| 6,736,957 B1 | 5/2004 | Forrow et al. | |
| 7,501,053 B2 | 3/2009 | Karinka et al. | |
| 7,754,093 B2 | 7/2010 | Forrow et al. | |
| 8,435,682 B2 | 5/2013 | Heller | |
| 2003/0014779 A1 | 1/2003 | Drotning | |
| 2005/0169219 A1* | 8/2005 | Serpa | H04L 29/12254 370/338 |
| 2009/0247857 A1* | 10/2009 | Harper | A61B 5/14532 600/365 |

(Continued)

FOREIGN PATENT DOCUMENTS

| | | | |
|---|---|---|---|
| WO | WO 2012/174538 A1 | 12/2012 | |
| WO | WO 2014/070471 A1 | 5/2014 | |

OTHER PUBLICATIONS

WO, PCT/US2015/031784 ISR and Written Opinion, Aug. 24, 2015.

*Primary Examiner* — Wen Huang
(74) *Attorney, Agent, or Firm* — One LLP

(57) ABSTRACT

Systems, devices, and methods are provided for the management of multiple sensor control devices and/or multiple reader devices in an in vivo analyte monitoring environment, and also for resolving conflicts when merging data collected by different reader devices.

20 Claims, 12 Drawing Sheets

(56) References Cited

U.S. PATENT DOCUMENTS

| | | | |
|---|---|---|---|
| 2010/0016700 A1* | 1/2010 | Sieh | A61B 5/14532 600/365 |
| 2011/0021143 A1* | 1/2011 | Kapur | H04L 63/0464 455/41.2 |
| 2011/0022411 A1* | 1/2011 | Hjelm | A61B 5/0015 705/2 |
| 2011/0213225 A1 | 9/2011 | Bernstein et al. | |
| 2012/0078071 A1 | 3/2012 | Bohm et al. | |
| 2013/0144134 A1 | 6/2013 | Lee et al. | |
| 2013/0210351 A1* | 8/2013 | Ling | H04W 4/008 455/41.1 |
| 2014/0005504 A1 | 1/2014 | Goodnow et al. | |
| 2014/0068742 A1 | 3/2014 | Phillips | |
| 2014/0233545 A1* | 8/2014 | Ferguson-Jarnes | H04W 12/08 370/338 |
| 2014/0313052 A1* | 10/2014 | Yarger | G06F 19/345 340/870.02 |
| 2015/0082408 A1* | 3/2015 | Yeh | A61B 5/4815 726/9 |
| 2015/0169857 A1* | 6/2015 | Wang | G06F 19/3468 604/67 |

\* cited by examiner

| READER DEVICE TYPE | USERS | SENSOR CONTROL DEVICES | ACTIVATION CAPABILITY | PAIR REQUIRED? | HISTORY RECENT | HISTORY FULL | OVERLAP | CONFIRMED JOIN CAPABILITY |
|---|---|---|---|---|---|---|---|---|
| DEDICATED-USE DEVICE FOR INDIVIDUAL WEARER (E.G., 120-1, 120-4) | ONE | ONE | YES | YES | YES | NO | NO | NO |
| SMARTPHONE FOR INDIVIDUAL WEARER (E.G., 120-3, 120-5) | ONE | MULTIPLE | YES | YES | YES | NO | YES | YES |
| SMARTPHONE FOR PARENT OF CHILD WEARERS (E.G., 120-2) | MULTIPLE | MULTIPLE | YES | YES | YES | NO | YES | YES |
| MULTIPLE MODES FOR CLINICAL SETTING, ALL DEVICE TYPES (E.G., 120-6) | | | | | | | | |
| MODE 1: INFREQUENT CONTACT WITH WEARERS | MULTIPLE | MULTIPLE | YES | NO | NO | NO | NA | NA |
| MODE 2: FREQUENT CONTACT WITH WEARERS | MULTIPLE | MULTIPLE | YES | YES | YES | NO | NO | NA |
| MODE 3: SCHEDULED CONTACT WITH WEARERS | MULTIPLE | MULTIPLE | YES | YES | NO | YES | YES | YES |
| MODE 4: NO CONTACT WITH WEARER | MULTIPLE | MULTIPLE | NA | NO | NO | YES | NA | NA |

FIG. 1D

MANAGEMENT OF MULTIPLE DEVICES WITHIN AN ANALYTE MONITORING ENVIRONMENT

CROSS-REFERENCE TO RELATED APPLICATIONS

This application claims the benefit of and priority to U.S. provisional application Ser. No. 62/001,343, filed May 21, 2014, which is incorporated by reference herein in its entirety and for all purposes.

FIELD

The subject matter described herein relates generally to the management of multiple devices within an analyte monitoring environment.

BACKGROUND

The detection and/or monitoring of analyte levels, such as glucose, ketones, lactate, oxygen, hemoglobin A1C, or the like, can be vitally important to the health of an individual having diabetes. Diabetics generally monitor their glucose levels to ensure that they are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost. For these and other reasons, needs exist for improved analyte monitoring systems, devices, and methods.

SUMMARY

A number of systems have been developed for the automatic monitoring of the analyte(s), like glucose, in a bodily fluid of a user, such as in the blood, interstitial fluid ("ISF"), dermal fluid, or in other biological fluid. Some of these systems include a sensor that can be at least partially positioned "in vivo" within the user, e.g., transcutaneously, subcutaneously, or dermally, to make contact with the user's bodily fluid and sense the analyte levels contained therein. These systems are thus referred to as in vivo analyte monitoring systems.

The sensor is generally part of a sensor control device that resides on (or in) the body of the user and contains the electronics and power supply that enable and control the analyte sensing. The sensor control device, and variations thereof, can be referred to as a "sensor control unit," an "on-body electronics" device or unit, an "on-body" device or unit, or a "sensor data communication" device or unit, to name a few.

The analyte data sensed with the sensor control device can be communicated to a separate device that can process and/or display that sensed analyte data to the user in any number of forms. This device, and variations thereof, can be referred to as a "reader device" (or simply a "reader"), "handheld electronics" (or a handheld), a "portable data processing" device or unit, a "data receiver," a "receiver" device or unit (or simply a receiver), or a "remote" device or unit, to name a few.

In vivo analyte monitoring systems can be broadly classified based on the manner in which data is communicated between the reader device and the sensor control device. One type of in vivo system is a "Continuous Analyte Monitoring" system (or "Continuous Glucose Monitoring" system), where data can be broadcast from the sensor control device to the reader device continuously without prompting, e.g., in an automatic fashion according to a broadcast schedule. Another type of in vivo system is a "Flash Analyte Monitoring" system (or "Flash Glucose Monitoring" system or simply "Flash" system), where data can be transferred from the sensor control device in response to a scan or request for data by the reader device, such as with a Near Field Communication (NFC) or Radio Frequency Identification (RFID) protocol.

Example embodiments of systems, devices, and methods are described that allow management of multiple sensor control devices and/or reader devices within an analyte monitoring environment. Some of these example embodiments involve the management of multiple reader devices in the collection of analyte data from a single sensor control device, while other example embodiments involve the management of analyte data collected by a single reader device from multiple sensor control devices, where the multiple sensor control devices belong to one user or multiple users. These and other example embodiments can be applied to a wide variety of situations involving complex interplay between devices and users, such as situations where multiple users are present, each having one or more sensor control devices, and where one or more reader devices are used to collect the analyte data from any or all of these sensor control devices. Also described are example embodiments that are capable of resolving conflicts between analyte data collected on multiple sensor control devices for a single user. Also described herein are example embodiments of managing issues involving the estimating of times, resolving conflicts in times, and determining that time events have occurred. Although not limited to such, the embodiments described herein are particularly suited to environments where the reader device is a smartphone.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 1D is a table describing capabilities for example embodiments of reader devices.

DETAILED DESCRIPTION

Figure 1B:
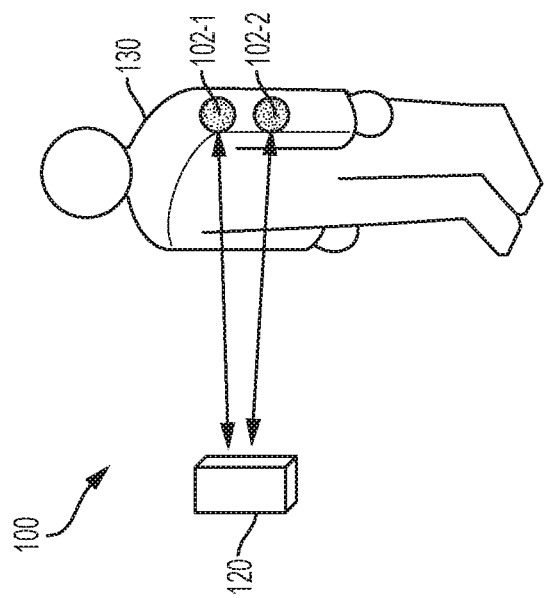
FIG. 1B is an illustrative diagram depicting an example embodiment of an in vivo analyte monitoring system having multiple sensor control devices communicating with a single reader device.

The present subject matter is not limited to the particular embodiments described, as such are only examples and may, of course, vary. Likewise, the terminology used herein is for the purpose of describing particular embodiments only, and is not intended to be limiting, since the scope of the present disclosure will be limited only by the appended claims.

The subject matter of this description pertains generally to the management of multiple sensor control devices and/or multiple reader devices within an analyte monitoring environment. In typical in vivo monitoring systems, each sensor control device is only allowed to interface with one reader device in order to restrict access to the user's data. That reader device is typically a dedicated-use device, i.e., one that was designed for the primary purpose of interfacing with a sensor control device, typically one built by the same manufacturer as that of the sensor control device. However, a reader device can also be in the form of a general purpose mobile communication device, such as a smartphone. The proliferation of smartphones makes it desirable for each user to have the option of using his or her smartphone to interface with the sensor control device in addition to, or instead of, a dedicated-use reader device.

The user's medical data is of a private nature and should be safeguarded from eavesdroppers, sometimes referred to as "snoopers." The identity of any reader device used to collect data from a sensor control device should therefore be verified prior to sending data to that reader device. Example embodiments described herein provide a manner by which a sensor control device can securely interface with multiple reader devices. Such a situation is depicted with respect to the in vivo analyte monitoring system 100 of FIG. 1A, where a user 130 uses a first reader device 120-1 and a second reader device 120-2 to wirelessly interface with a sensor control device 102 monitoring that user's analyte levels.

Sensor control devices 102 typically have a limited operating life and it is desirable for each reader device 120 to know when that operating life expires so as not to collect analyte data post-expiration. However, if reader device 120-2, for example, was not the same one used to activate sensor control device 102, then reader device 120-2 may not have data indicating how much of sensor control device 102's operating life has passed. Example embodiments described herein also provide for a manner of estimating (or learning) the remaining operating life of a sensor control device 102.

Figure 1A:
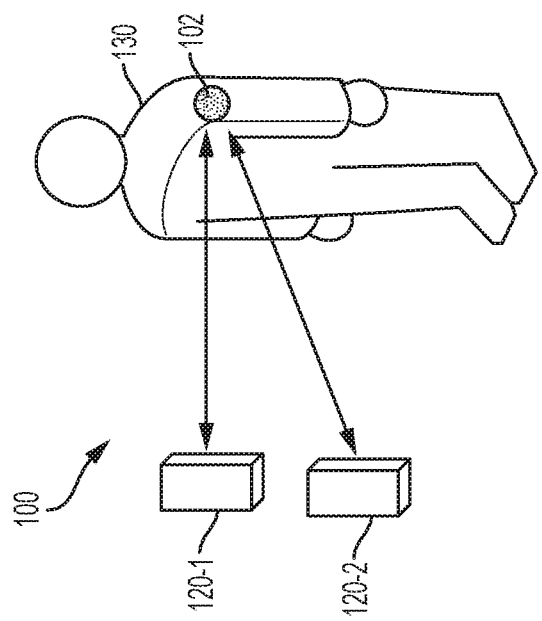
FIG. 1A is an illustrative diagram depicting an example embodiment of an in vivo analyte monitoring system having a sensor control device communicating with multiple reader devices.

It is also desirable to have a reader device 120 that can interface with multiple sensor control devices 102. Because of their limited operating life, typically much less than that of reader device 120, each sensor control device 102 must periodically be replaced by the user, which typically entails removing the expired sensor control device 102 from the user's body and replacing it with a newly activated sensor control device 102. For example, replacement may occur numerous times over the course of a year. In some cases, a user wearing a first sensor control device 102 may wish to activate a second sensor control device 102 prior to the expiration of the first so as not to lose any data during the second sensor control device's "warm-up" period (discussed in more detail herein). Accordingly, embodiments of reader devices 120 that can interface with multiple sensor control devices 102 in an overlap fashion are described herein. FIG. 1B depicts an example of system 100 where user 130 is wearing two activated sensor control devices 102-1 and 102-2, and uses a single reader device 120 to wirelessly interface with both in an overlapped, concurrent fashion (e.g., simultaneously or in a back-and-forth manner).

Figure 1C:
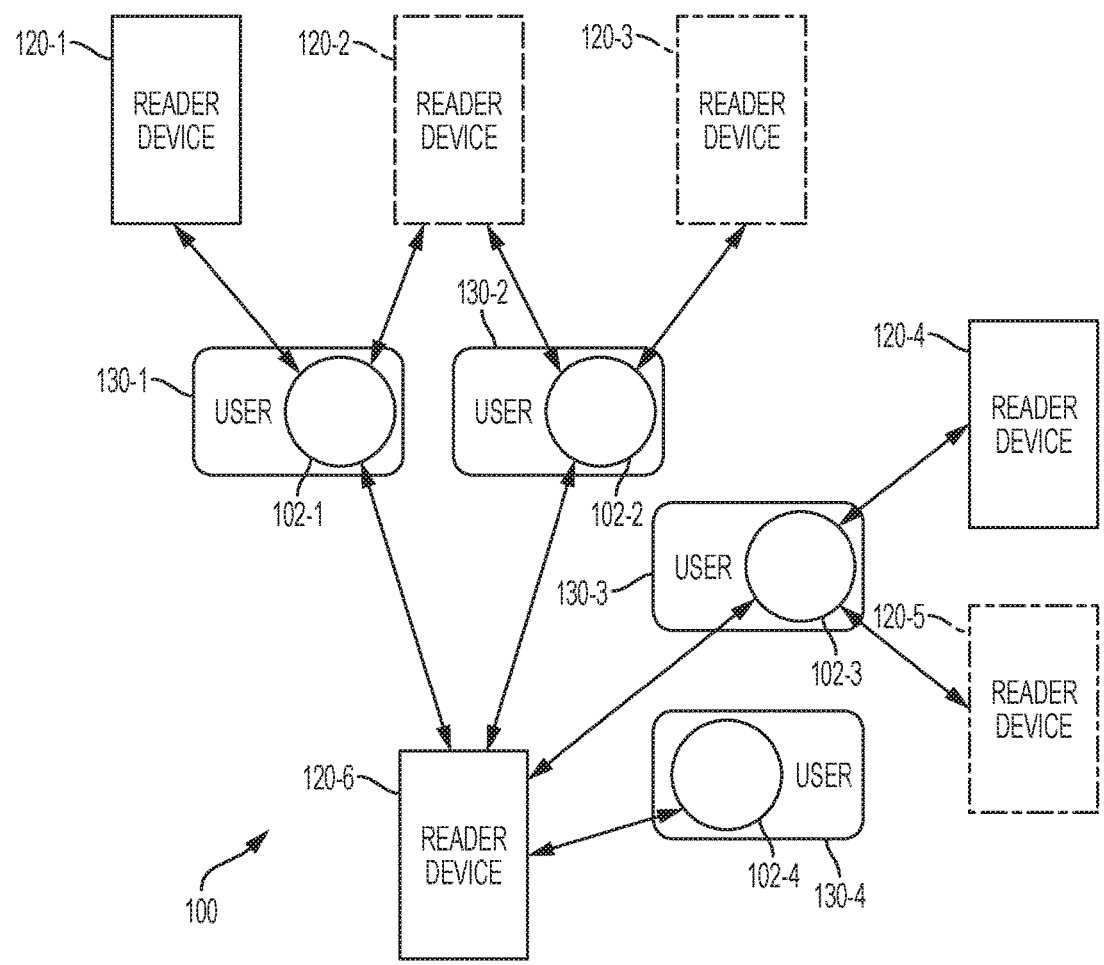
FIG. 1C is an illustrative diagram depicting an example embodiment of an in vivo analyte monitoring system having multiple sensor control devices communicating with multiple reader devices.

Still more complex environments are contemplated herein. FIG. 1C depicts an example of one such environment having a system 100 with four different sensor control devices 102-1 through 102-4, each being worn by a different user 130-1 through 130-4, respectively, and wirelessly interfacing with one or more reader devices 120-1 through 120-6. FIG. 1D depicts a table describing the types of reader devices 120-1 through 120-6 and summarizes their capabilities for comparison. Unless noted otherwise, the reader devices 120 described with respect to all of the embodiments herein can each be implemented in any of the reader device operating configurations described with respect to FIG. 1C and/or FIG. 1D.

In FIG. 1C, reader devices 120-1 and 120-4 are dedicated-use devices where each receives analyte data from only a single sensor control device 102 while that sensor control device 102 is active. This is indicated by "One" in the "Users" column and the "Sensor Control Devices" column of FIG. 1D.

Reader devices 102-1 and 120-4 can start-up or activate a sensor control device 102, as indicated by "Yes" in the "Activation Capability" column of FIG. 1D. In order to receive analyte data from sensor control device 102, reader devices 120-1 and 120-4 must first pair with the sensor control device 102 as indicated by the "Yes" in the "Pair Required?" column of FIG. 1D. Here reader device 120-1 activates and then pairs with sensor control device 102-1 and reader device 120-4 activates and then pairs with sensor control device 102-3 (see FIG. 1C). To pair, a reader device 120 will, for example, obtain an identifier (e.g., a serial number) from the sensor control device 102 and store it within its memory such that it can recognize that sensor control device 102 during later communications (where sensor control device 102 will again send its identifier). This can ensure that reader device 120 will only communicate with a single sensor control device 102 until the user activates and pairs with a second sensor control device 102 (which will then replace the first).

Reader devices 120-1 and 120-4 are programmed to collect and display recent analyte data for each user (see the "Yes" in the "Recent" "History" column of FIG. 1D), but not to collect and display full historical analyte data for each user (see the "No" in the adjacent "Full" "History" column). Recent history can be a history over the previous day, previous 12 hours, previous 8 hours, etc. Reader devices 120-1 and 120-4 are restricted from overlapping communication with a second sensor control device 102 in an initialization period, which is described in more detail below (see the "No" in the "Overlap" column). Reader devices 120-1 and 120-4 are also restricted from joining into communication with a sensor control device 102 that has been activated by another reader device 120 (see the "No" in the "Confirmed Join" column).

The remaining description will focus on those aspects and capabilities of other reader devices 120 that differ from the configuration example just described.

Reader devices 120-3 and 120-5 are not dedicated-use devices but rather smartphones each having a single-user software implementation that allows communication with only those sensor control devices 102 associated with a single user (as noted in the "Users" column of FIG. 1D). In FIG. 1C, reader device 120-3 communicates with sensor control device 102-2 of user 130-2, and reader device 120-5 communicates with sensor control device 102-3 of user 130-3. However, these reader devices 120-3 and 120-5 are programmed to allow the activation of a new sensor control device 102 for the same user 130 and still maintain communication with the older sensor control device 102 in a limited circumstance, for example, while the new sensor control device 102 is in an initialization period (see the description of overlapping communication herein). This is shown in FIG. 1D as operation being allowed with "Multiple" sensor control devices due to the allowed "Overlap" capability.

As shown in FIG. 1C, reader device 120-5 can join communications (e.g., by pairing) with a sensor control device 102-3 that has already been activated by a different reader device 120-4, so long as that sensor control device 102-3 belongs to the same user 130-3 as all of the other sensor control devices 102 with which reader device 120-5 is paired. Upon joining communication, reader device 120-5 can only communicate with that sensor control device 102-3 (as indicated by "One" in the sensor control device column of FIG. 1D). The same capability is present for reader device 120-3.

Moving to the next example, reader device 120-2 is not a dedicated-use device but rather a smartphone intended for use by, for example, a parent of multiple children each requiring analyte monitoring. Smartphone 120-2 has a multi-user software implementation that allows communication with sensor control devices 102-1 and 102-2 belonging to different child wearers 130-1 and 130-2, respectively. These capabilities are indicated by "Multiple" in the "Users" and "Sensor Control Devices" column of FIG. 1D. In this example, the remaining capabilities of FIG. 1D are the same as for reader devices 120-3 and 120-5.

Reader device 120-6 is an example of a reader device configured for a clinical setting where the operator is a medical professional. Reader device 120-6 can be any type (e.g., dedicated-use, smartphone, etc.) and can be configured to operate in a number of different modes depending on the particular situation.

The first mode is applicable to situations where infrequent in-person contact occurs with user/wearer 130 (e.g., once per week, once per two weeks, once per month, etc.). In these situations, the health care provider is primarily interested in the current analyte level of user 130. A number of these types of settings exist. For example, a physical therapy provider may see multiple patients (in-person) infrequently and want to evaluate their analyte levels prior to commencing therapy. The first mode is particularly applicable to sensor control devices 102 that have not yet expired (i.e., pre-expiration). In this first mode, reader device 120-6 can activate and interface with any number of sensor control devices 102 belonging to any number of users 130, and is not required to pair with those sensor control devices 102 in order to calculate and display the current analyte level for each user 130. Without pairing, reader device 120-6 is generally not able to associate sensor control devices 102 with a particular user, so reader device 120-6 does not log the recent history or the full history.

The second mode is applicable to situations where there is frequent in-person contact with user 130 (e.g., periodically throughout the day). A number of these types of settings exist, for example, in the case of a home care provider. This mode is similar to the example for reader device 120-2 used with a parent of multiple children. This mode is particularly suitable for sensor control devices 102 that have not yet expired. In this mode, reader device 120-6 can activate and interface with any number of sensor control devices 102 belonging to any number of users 130. In this example, reader device 120-6 must pair to associate a user with sensor control device 102. Reader device 102-6 logs the recent history so that it can be reviewed for each user 130. Downloading the full historical data is not permitted as it can be a lengthy process that drains the power source of sensor control device 102, especially if reader device 120-6 is downloading the entire history at one time.

The third mode is applicable to scheduled in-person contact with user 130 (e.g., commonly infrequently, but also frequently). The health care provider is interested in the current analyte level, as well as in the historic analyte levels. A number of these types of settings exist, for example a primary physician or a health and wellness coach. This mode is particularly suitable for sensor control devices 102 that have not yet expired. In this mode, reader device 120-6 can activate and interface with any number of sensor control devices 102 belonging to any number of users 130. Reader device 120-6 pairs to associate a user 130 with sensor control device 102. Reader device 120-6 logs the recent history so that it can be reviewed for each user 130. Reader device 120-6 also downloads the full historical data to have as much historic information as possible when evaluating and counseling the user 130.

The fourth mode requires no in-person contact with user 130. Since the user 130 is not present, the health care provider is only interested in the historic analyte levels. A number of these types of settings exist, for example a return mail service. Sensor control device 102 will have normally expired when this mode is used. There is also no need to activate nor pair with sensor control devices 102 in this mode and thus those functions are not present. There is also no need for the recent history because it is duplicated in the full history. Reader device 120-6 does download the full history.

The sensor control device capability drives some of the mode differentiators. For example a low cost sensor control device 102 may not have full history capability. A reader device 120 may include more than one mode depending on the type of sensor control device 102. For example a reader device 120 can employ the second mode with a low cost sensor control device 102, and can employ the third mode with a full history capable sensor control device 102.

As mentioned above, certain smartphone reader devices 120 can join with a sensor control device 102 that has already been activated by a different reader device 120. See FIG. 1C, for example, where smartphone reader device 120-2 joins into communication with sensor control device 102-1 after it has already been activated by dedicated-use reader device 120-1.

Figure 2:
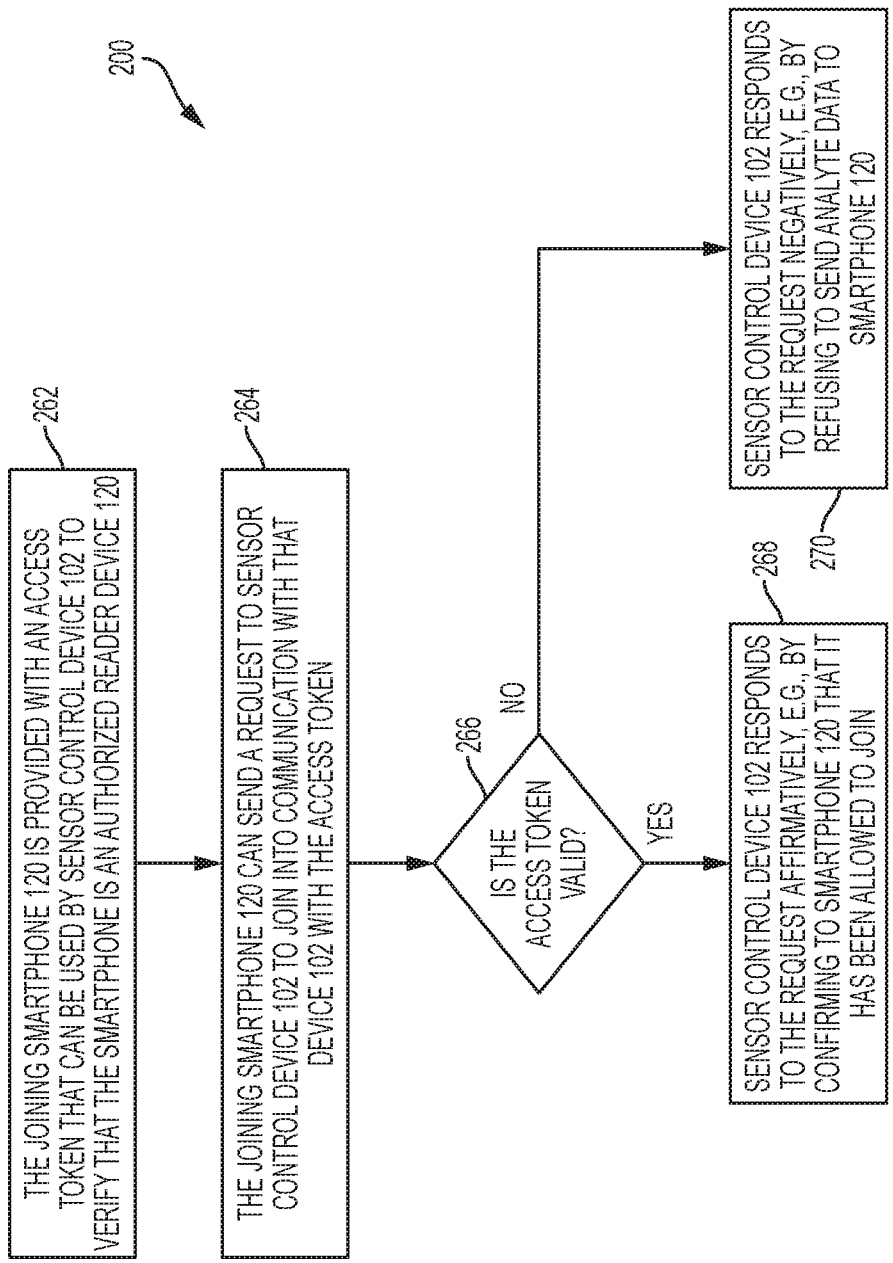
FIG. 2 is a flow diagram depicting an example embodiment of a method of joining a reader device with a sensor control device that has already been activated.

FIG. 2 is a flow diagram depicting an example embodiment of a method 200 of joining a reader device 120 with a sensor control device 102 that has already been activated. Although not limited to such, in this example the joining reader device 120 is a smartphone. At 262, the joining smartphone 120 is provided with an access token that can be used by sensor control device 102 to verify that smartphone 120 is an authorized reader device, e.g., a reader device 120 associated with the wearer of sensor control device 102. The access token can be any string of characters that is suitable for use as a passcode. The access token can be random or pseudorandom and can be comprised of letters, numbers, and/or symbols. The access token can be provided by the sensor control device manufacturer or can be set by the user.

If the access token is set by the user, it is desirable to accomplish this when the sensor control device 102 is originally activated for security purposes. Upon powering up sensor control device 102, the user would enter the string of characters chosen (to act as the access token) into the activating reader device 120 (e.g., using any of the reader's user interface features). That chosen access token can then be hashed, stored within smartphone 120, and sent to sensor control device 102, which can store the token to an onboard writable memory (e.g., memory 253 described with respect to FIG. 6C). Any further communications from the activating reader device 120, such as a request for measured analyte data (sometimes referred to as a "scan"), can include the hashed access token. Upon receipt, sensor control device 102 can compare the received access token to the one stored in memory and, if the two access tokens match, sensor control device 102 can respond appropriately, such as by sending the user's measured analyte data or any other requested confidential data, to the activating reader device 120.

Since the user knows the selected access token, the user can then enter the selected access token at step 262 into a second reader device 120 that is joining communication with the already activated sensor control device 102.

If the access token is provided by the manufacturer (or a similar entity), then it is desirable for the access token to be stored within any writable or read-only memory of sensor control device 102 at the time of manufacture.

That same access token is then also to be provided to smartphone 120 at 262, in any of a number of ways. For example, the packaging for a component of in vivo analyte monitoring system 100 can have the access token printed thereon. The access token can be printed in human-readable form, e.g., on a holographic label, such that the user can input the access token directly into smartphone 120 in step 262. This may, for example, be in response to a prompt by a user interface application operating on smartphone 120.

The access token can also be printed in machine-readable form, such as in the form of a barcode. The barcode can be a one-dimensional barcode, two-dimensional barcode, or three-dimensional barcode and can be of any format (QR code, data matrix, maxicode, aztec code, QR code, etc.). Printed indicia other than barcodes can be used as well. In such an example, an optical scanner (e.g., a camera) of the reader device can optically scan the barcode to provide the access token to the reader device in step 262.

In another example, the access token is stored in an RFID (or NFC) label or tag accompanying the packaging and can be read using an RFID (or NFC) scanner that is part of smartphone 120. Other machine-readable formats can be used to obtain the access token from the packaging. The packaging itself can be a container for any part of system 100 that is supplied to the user. For example, the packaging can be a container for sensor control device 102 alone, a container for multiple sensor control devices 102 (e.g., a multi-pack), a container for sensor control device 102 in combination with an inserter 150 (see FIG. 6A herein), a container for inserter 150 alone. The "packaging" can also refer to inserts, labels, instructions, manuals, or the like that are contained within or otherwise shipped with system 100.

In yet another example, the access token can be stored in the memory of the activating reader device 120 and either displayed to the user (such that the user can then manually enter the access token into the joining smartphone 120), or electronically communicated to the joining smartphone 120, with a wired connection (e.g., USB) or wireless connection (e.g., Bluetooth, Bluetooth Low Energy, NFC, RFID, or an internet or other high bandwidth connection).

In all of these embodiments, the provision of the access token to smartphone 120 can be done at a time of the user's choosing or in response to a prompt to do so by reader device 120.

Referring back to FIG. 2, the joining smartphone 120, now having received the access token at 262, can send a request to sensor control device 102 to join into communication with that device 102 at 264. This request may be purpose-specific, i.e., one generated for the primary purpose of joining with sensor control device 102, or the request may be a standard data request (such as a request for measured analyte data) that is interpreted by sensor control device 102 as not only a request for the data but also a request to join into communication. The request can include the hashed access token. Upon receipt of the request, at 266 sensor control device 102 can compare the access token stored in memory to the received access token to determine if it is valid. At 268, if the two access tokens match, sensor control device 102 can confirm to smartphone 120 that it has been allowed to join, or can send the user's measured analyte data or any other requested confidential data to smartphone 120, or otherwise. If the two tokens do not match, then at 270 sensor control device 102 can send a notification of such to reader device 120 and refuse to respond with the requested data.

In some embodiments, each communication sent by a reader device 120 to a sensor control device 102 will not only include the access token but also a unique identifier of that reader device 120. Sensor control device 102 can maintain a list of approved reader devices 120 and can also be programmed to allow communications with only a limited number of reader devices 120 at any time, e.g., as a safeguard against multiple surreptitious joins should the access token become public. In other embodiments, sensor control device 102 will respond to any request for data from a reader device 120 so long as that request contains the correct access token, regardless of the identity of the requesting device 120 and regardless of the number of devices 120 with which sensor control device 102 has already transmitted confidential data to.

The operating life of a sensor control device 102 is typically based upon a maximum duration of time over which sensor 104 can reside within the user's body and continue to provide accurate measurements. In some embodiments, sensor control device 102 will have an end of life count ($C_{MAX}$) stored in memory. Sensor control device 102 can regularly increment an on-board counter during its life and terminate its operation once the counter reaches the $C_{MAX}$ limit. The $C_{MAX}$ limit can assume worst case clock error and temperature drift scenarios to ensure that sensor control device 102 does not operate past the intended operation life. If the activating reader device 120 has a reliable clock and records the activation time of sensor control device 102, then in some embodiments the clock of reader device 120 can be used to monitor the length of time at which sensor control device 102 has been active and cause termination of sensor control device 102 when the full life has been reached. If no reader device 120 causes termination then sensor control device 102 will do so itself once it reaches $C_{MAX}$.

Reader devices 120 may be permitted to join communication with sensor control device 102 at any time during the life of sensor control device 102. In certain embodiments though, reader devices 120 may only be permitted to join communication with a sensor control device 102 during a predetermined time period after sensor control device 102 is initially activated (e.g., a time significantly shorter than the operating life). The time at which initial activation occurs is the "activation time" and generally refers to the time that the sensor control device 102 is powered on (or exits any low power or sleep state) and begins initialization for measuring analyte data of the wearer. Permitting joining within this predetermined time period increases the likelihood that the pairing is authorized and protects against "snooping." Use of the predetermined time period can also ensure that the joining reader device 120 is paired early in the operating life of the sensor control device 102 so that the joining reader device 120 will have a more accurate estimate of the activation time of device 102 (e.g., typically only the activating reader device 120 knows the actual activation time). As mentioned, reader device 120 may be programmed so as not to request or accept analyte data from a sensor control device 102 after that device 102 has exceeded its operating life.

In some of these embodiments, the predetermined time period is the same as an initialization time period, sometimes referred to as a "warm-up" period, for sensor control device 102. The initialization period can allow the chemistry of sensor 140 to reach equilibrium and stabilize after activation. The display of real-time glucose values is delayed until after this initial period of instability.

The initialization time period is less than the operating life of device 102, and in many embodiments is substantially less than the operating life. The predetermined time period can be 15% of the operating life, 10% of the operating life, 5% of the operating life, or 1% of the operating life, to name a few examples. In one example, sensor control device 102 has an operating life of 14 days and the predetermined time period is one (1) hour.

Reader device 120 can include software programming for estimating the activation time of sensor control device 102. An example of a formula (1) for this estimation is below.

$$T_{EST} = T_{CUR} - [C*I*(L_{FC}/L_{sTD})*D] \qquad (1)$$

Here, $T_{EST}$ is the estimated activation time of sensor control device 102 and $T_{CUR}$ is the current time of reader device 120. C is the current count of sensor control device 102, which can be the value of a sequential counter that is updated after the passage of a count time interval (I). Interval (I) can be a fixed or set time interval between counter increments, or can be realized using a regularly repeating, or pseudo-regularly repeating data collection interval that occurs within sensor control device 102. Other approaches can be used as well.

But in many embodiments the clock may have a lower accuracy and may drift, such as due to temperature. In these cases the count interval for each sensor control device 102 can be measured by the manufacturer to arrive at a device-specific correction value ($L_{FC}$), e.g., a measured clock frequency of the particular sensor control device 102. The clock offset can be corrected using the correction value along with an ideal value ($L_{STD}$) for that class or model of sensor control device 102, e.g., the standard clock frequency.

D is a factor that corresponds to the maximum (or worst-case) drift of the clock of sensor control device 102. In an ideal situation, sensor control device 102 would remain at the same temperature as when $L_{FC}$ was calculated. But if, for example, the temperature was higher than when $L_{FC}$ was calculated, then the oscillator will have run slow and C will under-represent the actual number of minutes that have transpired. D is determined by the sensor control device clock characteristics and will typically be a little greater than one (1.00) to ensure that the time since activation is not underestimated. In some embodiments, real-time temperature readings can be taken and relied upon to scale (reduce or increase) D to more accurately reflect the conditions experienced by sensor control device 102, and thus produce a more accurate estimation.

In certain embodiments, C is incremented approximately every one minute as determined by a clock (e.g., a crystal oscillator or an RC oscillator) of sensor control device 102. In embodiments where the clock accuracy is very good and is minimally subject to variation, $T_{EST}$ is $T_{CUR}$ minus the number of sensor counts (C) times the count interval (I) (e.g., one minute, two minutes, etc.).

After joining, sensor control device 102 will communicate the aforementioned information (e.g., C, $L_{FC}$, $L_{STD}$) required by reader device 120 to perform the activation time estimate. This time estimate (or an estimated duration of time that has passed since activation) can then be used to determine the remaining operating life for sensor control device 102. If the sensor control device clock is perfect and the temperature remains constant then equation (1) is simplifies to equation (2) below.

$$T_{EST} = T_{CUR} - [C*I] \qquad (2)$$

If reader device 120 scans sensor control device 102 after the end of the full life but before $C_{MAX}$, then reader device 120 will only use the analyte data up to the end of the operating life as determined by the real activation time or the earlier estimated activation time.

The use of equation (1) to estimate the remaining operating life for the sensor control device 102 can incorporate the worst case scenario for clock drift (as described above), in which case the estimated termination will likely be premature, or early, assuming that the sensor control device 102 does not actually experience worst case conditions. In certain embodiments, the maximum error ($T_{EST}$-$T_{ACT}$) is estimated by formula (3) below.

$$\text{MaximumError} = T_{EST} - T_{ACT} = S*(L_{FC}/L_{STD})*(D-1) \quad (3)$$

Table 2 shoes error values based on a 14 day operating life. The values in Table 2 are maximum values, and in practice will typically be about half (or less) of these maximums. As can be seen here, the longer into the operating life one waits to join reader device 120 with sensor control device 102, the greater the maximum error will be, and the shorter the operating life will become if one wishes to safeguard against inadvertently using device 102 after its expiration. Nevertheless, even if reader device 120 joins 14 days into the operation of sensor control device 102, the premature termination of device is only about 155.7 minutes, or less than three hours.

TABLE 2

| Age (days) of Sensor Control Device 102 | Sample Number | Early Expiration (minutes) |
| --- | --- | --- |
| 0 | 0 | 0.0 |
| 1 | 1440 | 11.1 |
| 2 | 2880 | 22.2 |
| 3 | 4320 | 33.4 |
| 4 | 5760 | 44.5 |
| 5 | 7200 | 55.6 |
| 6 | 8640 | 66.7 |
| 7 | 10080 | 77.8 |
| 8 | 11520 | 89 |
| 9 | 12960 | 100.1 |
| 10 | 14400 | 111.2 |
| 11 | 15840 | 122.4 |
| 12 | 17280 | 133.5 |
| 13 | 18720 | 144.6 |
| 14 | 20160 | 155.7 |

As an alternative to estimation using equation (1), the activating reader device 120 can communicate the actual activation time (or current duration of operation) to the non-activating reader device 120 over a wireless or wired data communication link.

Referring back to the initialization time period, as mentioned it may be desirable for a user to continue to collect data from an older sensor control device 102 while initializing a newer sensor control device 102. This will allow the user to continue to monitor his or her analyte level with the older sensor control device 102 while the newer sensor control device 102 transitions through the initialization time period (e.g., "warms up"). In those cases, the reader device 120 that was used to activate the older sensor control device 102 may also be used to activate the newer sensor control device 102 and may need to "overlap" communication with both devices 102 (similar to the situation of FIG. 1B).

In some embodiments, the software of reader device 120 will treat the older sensor control device 102 as the primary sensor control device. The primary sensor control device will be presented to the user on the reader device display as the "active" control device 102 or the sensor control device 102 that is currently being relied upon to provide analyte data to the user. The reader device 120 can select the newer sensor control device 102 as the primary sensor control device once reader device 120 receives data indicative of the current analyte level of the user after exiting the initialization period. For example, the first time that the user scans the newer sensor control device 102 after that sensor control device 102 has exited the initialization or warm-up period, the reader device 120 will select the newer sensor control device 102 as the primary sensor control device and display it as such to the user.

Analyte data collected from the older sensor control device 102 can be distinguished from analyte data collected from the newer sensor control device 102 based on an identifier that is unique to each sensor control device 102 and communicated with that sensor control device's analyte data. The identifier, referred to herein as a sensor ID, can be any string of characters (e.g., numbers, letters, or symbols) that uniquely identifies the associated sensor control device 102 within system 100. While the sensor ID can be unique in an absolute sense, it is sufficient for the sensor ID to be substantially unique among the set of sensor control devices 102 that may be used with the user's reader devices 120.

In many embodiments it is desirable for a reader device 120 to collect analyte data from multiple users, for example, a care provider monitoring analyte levels for the elderly or a parent monitoring analyte levels for several children. In these embodiments, the data collected by the reader device operator for each user is associated to that user with a user identifier, or user ID. The user identifier can be any string of characters that uniquely identifies the user. The user identifier can be non-random, random or pseudorandom and can be comprised of letters, numbers, and/or symbols. As with the sensor ID, the user identifier can be unique in an absolute sense, it is sufficient for the sensor ID to be substantially unique among the set of sensor control devices 102 that may be used with the user's reader devices 120.

Figure 3:
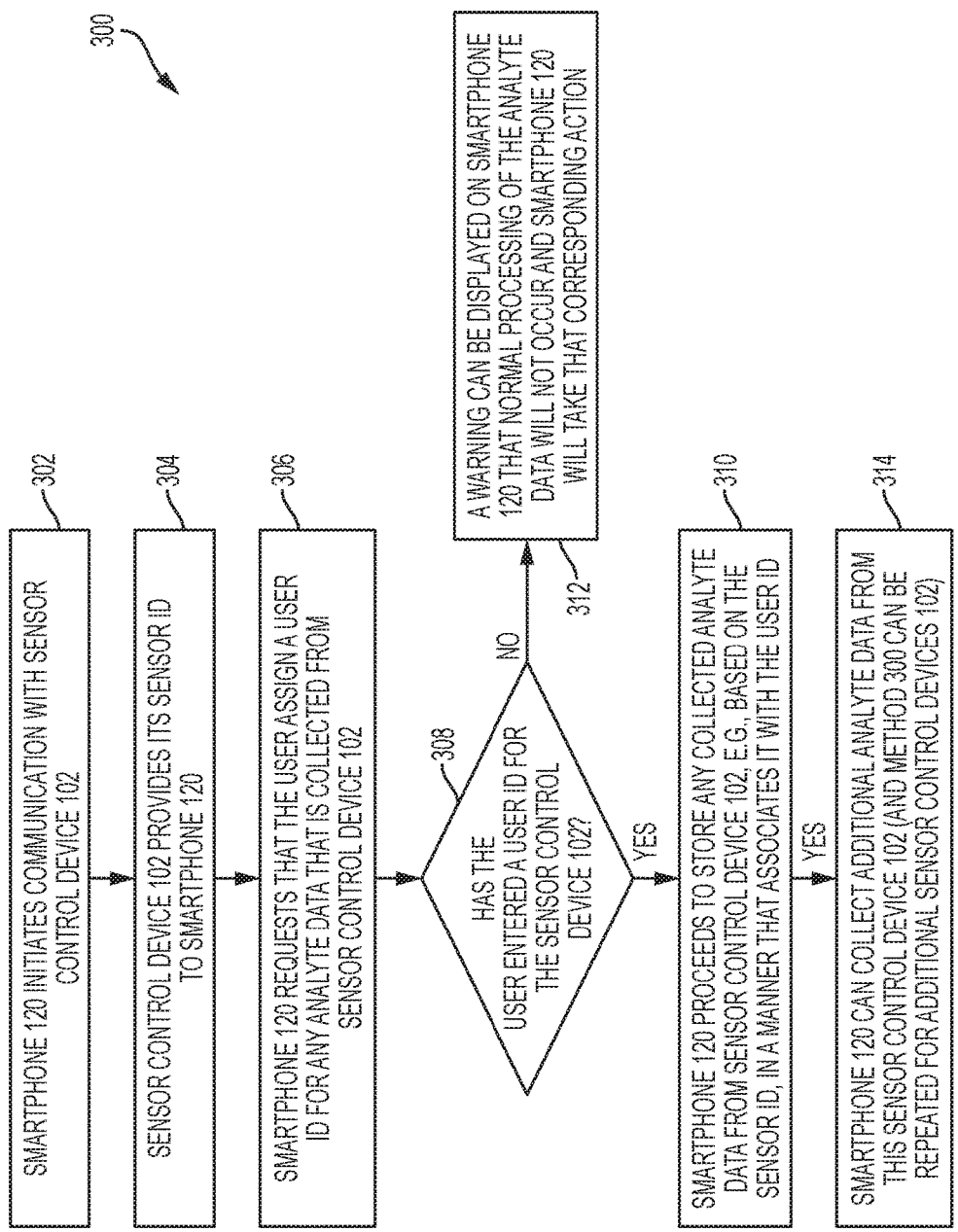
FIG. 3 is a flow diagram depicting an example embodiment of a method of using a reader device to collect analyte data from multiple users where each user's data is associated with a user identifier.

FIG. 3 is a flow diagram depicting an example embodiment of a method 300 of using a reader device 120 to collect analyte data from multiple users where each user's data is associated with a user identifier. In this example, reader device 120 is a smartphone. At 302, smartphone 120 initiates communication with sensor control device 102. This can be a request to pair with sensor control device 102 or a request for analyte data from sensor control device 102. At 304, sensor control device 102 provides its sensor ID to smartphone 120. At 306, smartphone 120 requests that the user assign a user ID for any analyte data that is collected from the sensor control device 102. This would be accomplished with a prompt displayed to the user on a display 122 (see FIG. 6A) of smartphone 120, but could also be performed at the initiative of the user. At 308, the software of smartphone 120 determines whether the user has entered a user ID for the sensor control device 102 and, if so, then smartphone 120 proceeds to store any collected analyte data from sensor control device 102, e.g., based on the sensor ID, in a manner that associates it with the user ID at 310.

If the user fails to enter a user ID, then, at 312, a warning can be displayed on the smartphone 120 that normal processing of the analyte data will not occur and smartphone 120 will take that corresponding action. This can include refusing to display the current analyte data to the user, refusing to save the analyte data on smartphone 120 (which also would prevent the display of historical analyte data), both aforementioned actions, or other actions.

At 314, smartphone 120 can collect additional analyte data from this sensor control device 102, or from a second sensor control device 102. If smartphone 120 does not have a user ID associated with that second sensor control device 102, then, after initiating communication with the second sensor control device 102, smartphone 120 can repeat steps 304 through 308 as needed for that second sensor control device 102, with outcomes 310 or 312. This process can be repeated for any number of subsequent sensor control devices 102.

In cases where a reader 120 communicates with and collects analyte data from multiple sensor control devices 102, the smartphone software has the capability to retrieve a list of all active and inactive sensor control devices with each one's associated activation times, expiration times, and times at which the sensor control device exits the initialization period. In some embodiments, an API can execute a search (e.g., SQL) that returns the results in a data structure (e.g., list, table, array, etc.).

In cases where a reader 120-2 collects data from a sensor control device 102 activated initially by another reader 120-1, that data collection functionality can be independently permitted or prevented. In other words, the capability of reader 120-2 to read data from the already active sensor control device can be configured by the user as permissible or not permissible.

Each reader device 120 can have informatics software stored thereon that allows the display of historical analyte data and that includes features or tools to assist in the analysis of the historical analyte data. The informatics software could also be installed on a remote terminal 170 (described with respect to FIG. 6A below), e.g., a personal computer or a tablet, or could be hosted by a trusted network (not shown), such as an internet server or other computer system. In these examples the user would upload the analyte data from the collecting reader device(s) 120 to remote terminal 170 or a trusted server prior to acting upon that data with the informatics software. One example of an informatics software program is the commercially available GLOOKO application.

Figure 4A:
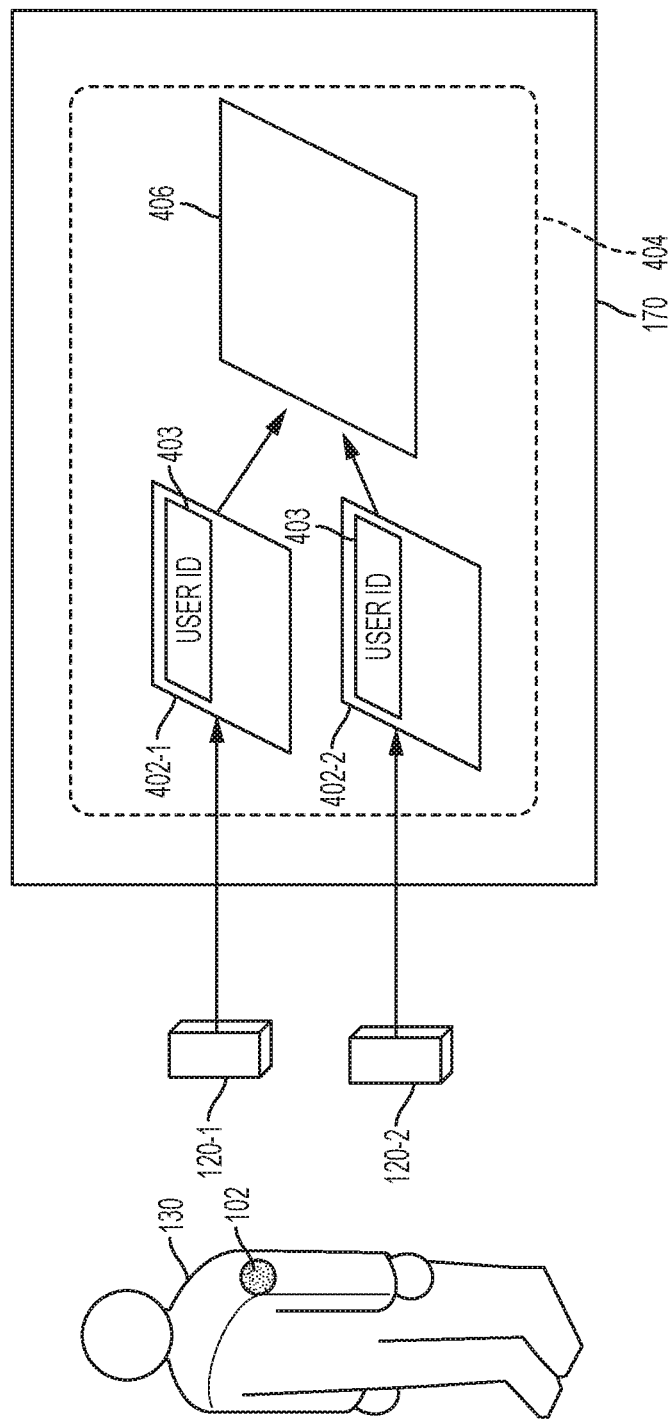
FIG. 4A depicts an example embodiment of a in vivo analyte monitoring system where a first reader device is used to activate a sensor control device on the body of a user.

Regardless of where the informatics software is installed, in the embodiments described herein a user can collect analyte data from a single sensor control device 102 using multiple different reader devices 120, and this can lead to conflicts when providing the data to the informatics software. FIG. 4A depicts an example embodiment of a system 100 where a first reader device 120-1 is used to activate a sensor control device 102 on the body of a user 130. That reader device 120-1 is used to collect analyte data from sensor control device 102. User 130 also uses a second reader device 120-2 to collect analyte data from sensor control device 102. The collected analyte data is stored on reader device 120-1 as a data compilation (or data set) 402-1 and on reader device 120-2 as a data compilation 402-2. Both data compilations 402-1 and 402-2 are provided (e.g., uploaded) to informatics software 404 in a manner that associates them with the sensor ID and the user's ID 403. (While it is possible to associate data compilations 402-1 and 402-2 with just the sensor ID, this does not allow the user's historical data to be analyzed across multiple sensor control devices 102.) The user ID may be stored and transferred in a data file separate from the raw analyte data and sensor ID value, which may facilitate HIPAA compliance and facilitate the creation of a map of user ID's to sensor ID files by software 404.

Software 404 then merges the data compilations 402-1 and 402-2 into a merged data compilation 406, which may also include historical analyte data for the user taken from other sensor control devices 102, with all such data linked together with the user ID 403.

Because different reader devices 120-1 and 120-2 were used, it is possible that one or more conflicts exist between data compilations 402-1 and 402-2, which in turn can make the merger process difficult. One such conflict can result from non-synchronized clocks, i.e., the time setting of reader device 120-1 may not match the time setting of reader device 120-2. For example, the time setting for reader device 120-1 may have been set by the user while the time setting for reader device 120-2 may be sourced from a telecommunications network, there may be phase drift with the clock of one of the reader devices 120-1 and 120-2, or the two reader devices 120-1 and 120-2 may be set to different time zones as the result of travel, and so forth. The sensor ID and sensor count (or sensor sample number) are sourced from sensor control device 102 itself and can be used to align or otherwise overlay the two data compilations 402-1 and 402-2. But conflicts can arise in the time stamps accompanying the two data compilations 402-1 and 402-2 since they are generated by reader devices 120-1 and 120-2, respectively.

Figure 4B:
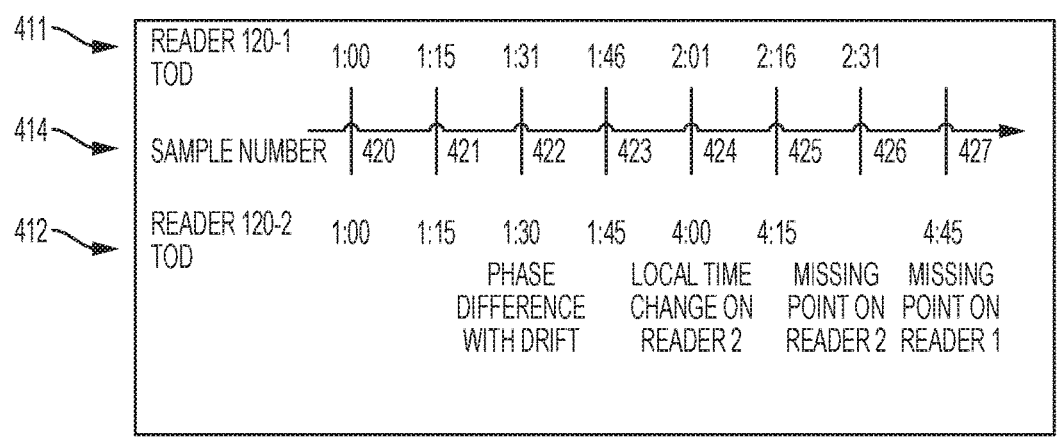
FIG. 4B depicts an example situation where differences occur between time stamps of a first reader device and time stamps of a second reader device corresponding to a sequence of sensor samples.

FIG. 4B depicts an example situation where differences occur between time stamps 411 of reader device 120-1 and time stamps 412 of reader device 120-2 for a sequence of sensor samples 414. A first time difference appears at sample number 422 where reader device 120-1 has drifted ahead of reader device 120-2 by one minute. This one minute offset carries through the remainder of the sample numbers that are shown, but a further difference is introduced at sample number 424 when a local time change occurs at reader device 120-2.

Conflicts may also arise in merging the data if there are differences in the filtering or smoothing functions performed by reader devices 120-1 and 120-2. In some embodiments, different reader devices 120 can calculate and record different results for a particular raw analyte data sample recorded by a sensor control device 102. Certain filtering algorithms executed by a reader device 120 can use other analyte measurements occurring before and/or after the particular data sample in order to provide additional context with which to determine what the best analyte value is for the particular data sample.

Referring back to FIG. 4B, both reader devices 120-1 and 120-2 have collected the raw data for sample numbers 420-425, but reader device 120-1 has only collected the raw data for sample number 426 and not for sample number 427. Conversely, reader device 120-2 has only collected the raw data for sample number 427 and not for sample number 426. If, when determining the analyte level that corresponds to the raw data of sample 425, each reader device 120-1 and 120-2 uses samples occurring both before and after sample 425, then reader devices 120-1 and 120-2 will be working with different data, as reader device 120-1 does not have sample 427 and reader device 120-2 does not have sample 426. The filtering algorithms on each reader device 120 may interpret sample 425 differently when converting to, e.g., the current analyte value or current analyte rate of change.

Software 406 can reconcile these conflicts (e.g., time, filtering) in a number of ways. In some embodiments, software 406 can request that the user identify which reader device 120 should be used as a "master" within resolving conflicts. For example, if there is a conflict between data compilations 402-1 and 402-2, then the user can select either reader device 120-1 or reader device 120-2 to act as the master, in which case all conflicts will be resolved in favor of the master. For example, the master's time setting can be used in place of the non-master's; the master's filtered data or smoothed data can be used in place of the non-master's; the master's filtering algorithm or smoothing algorithm can be used on the data of the non-master device to generate new data; or all combinations thereof. In other embodiments, software 406 can default to a particular class of reader device 120 as the master device. For example, if only one smartphone reader device 120 was used, then that smartphone device will be designated the master by default since it has a network synchronized clock. In alternative embodiments, software 406 can default to the activating reader device 120 as the master device. In still other embodiments, a dedicated-use activation device that can synchronize with a local network clock can serve as the master. The designation of this type of device (or a smartphone) as the master can be most useful when the other reader device 120 is a device that has not been synchronized to a network clock (e.g., some dedicated-use type devices).

Current time settings often vary between devices due to clock drift, changes by the user, e.g., as a result of travel between time zones, daylight savings time, correcting incorrect times, and the like. Because of these variances, conflicts in recorded time within an analyte dataset often occur. While these conflicts can result from multiple readers 120 taking data from a single sensor control device 102, or a single reader 120 taking data from multiple sensor control devices 102, they can also occur when a single reader device 120 takes data from a single sensor control device 102.

For example, when a smartphone reader device 120 receives data indicative of an analyte level from sensor control device 102 (e.g., after performing a scan), reader device 120 can timestamp that data using the current time taken from the reader's clock, which may be the same smartphone system clock that provides or sources the current time for display to the user. If the user changes time zones immediately subsequent to a scan and the system clock is changed accordingly, then it is possible that the next sensor scan by the smartphone reader device 120 will result in data that has the same or an earlier timestamp (independent of the time zone).

Consider a user that flies from New York to Los Angeles and, during the flight, scans sensor control device 102 at 7 am, 8 am, 9 am, 10 am, 11 am and 12 pm Eastern Standard Time (EST). A smartphone reader 120 that timestamps collected analyte data without reference to the time zone will show data collections at those times but without noting EST. Shortly after landing the time on the smartphone reader 120 is corrected to 10 am pacific standard time (PST) and the user performs a scan collecting analyte data at every hour thereafter, resulting in analyte data with timestamps of 10 am, 11 am, 12 pm, 1 pm, 2 pm, 3 pm, and so forth. The resulting analyte data will overlap and there will be two values for 10 am, 11 am, and 12 pm.

Figure 5A:
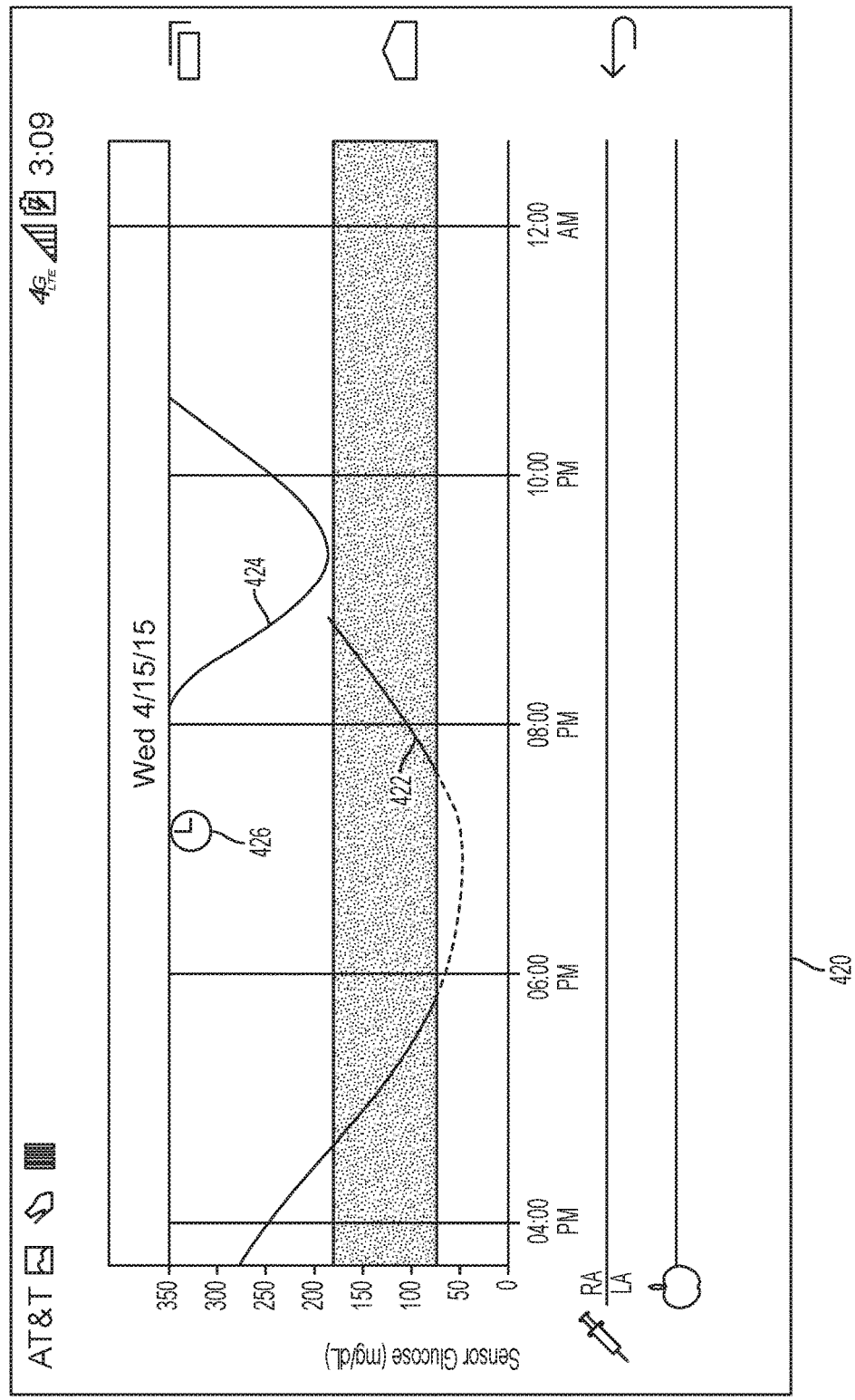
FIG. 5A is an example of an analyte data versus time graph having a time change icon thereon.

Display of this analyte data to the user in overlapping fashion in a graph or logbook can be confusing without some indication that a time change occurred. FIG. 5A is a sample screen 420 that graphs analyte date (Y axis) versus time (X axis) that can be shown on display 122 of reader device 120 (smartphone, dedicated use, or otherwise). Here, from approximately 8:00 pm to 8:45 pm an overlap occurs between analyte level curves 422 and 424. Reader device 120 brings this to the user's attention by display of a time change icon 426, which informs the user that the overlap was a result in clock settings that were changed.

Automatic detection of the time change by a smartphone reader 120 can be difficult. For one, a glucose monitoring application that runs on top of the smartphone's operating system (OS), e.g., Windows, Mac OSX, Android, iOS, is not directly informed when the system time is changed. The system uptime is available but it is not a true monotonic clock (i.e., a clock that constantly moves forward and does not cease or reset) since it resets each time the smartphone is rebooted, turned off, runs out of power, etc. Furthermore, even if time changes are detected, the glucose monitoring software must identify only those time changes that are significant for the purposes of data presentation with a time change icon or other time change indicator.

Figure 5B:
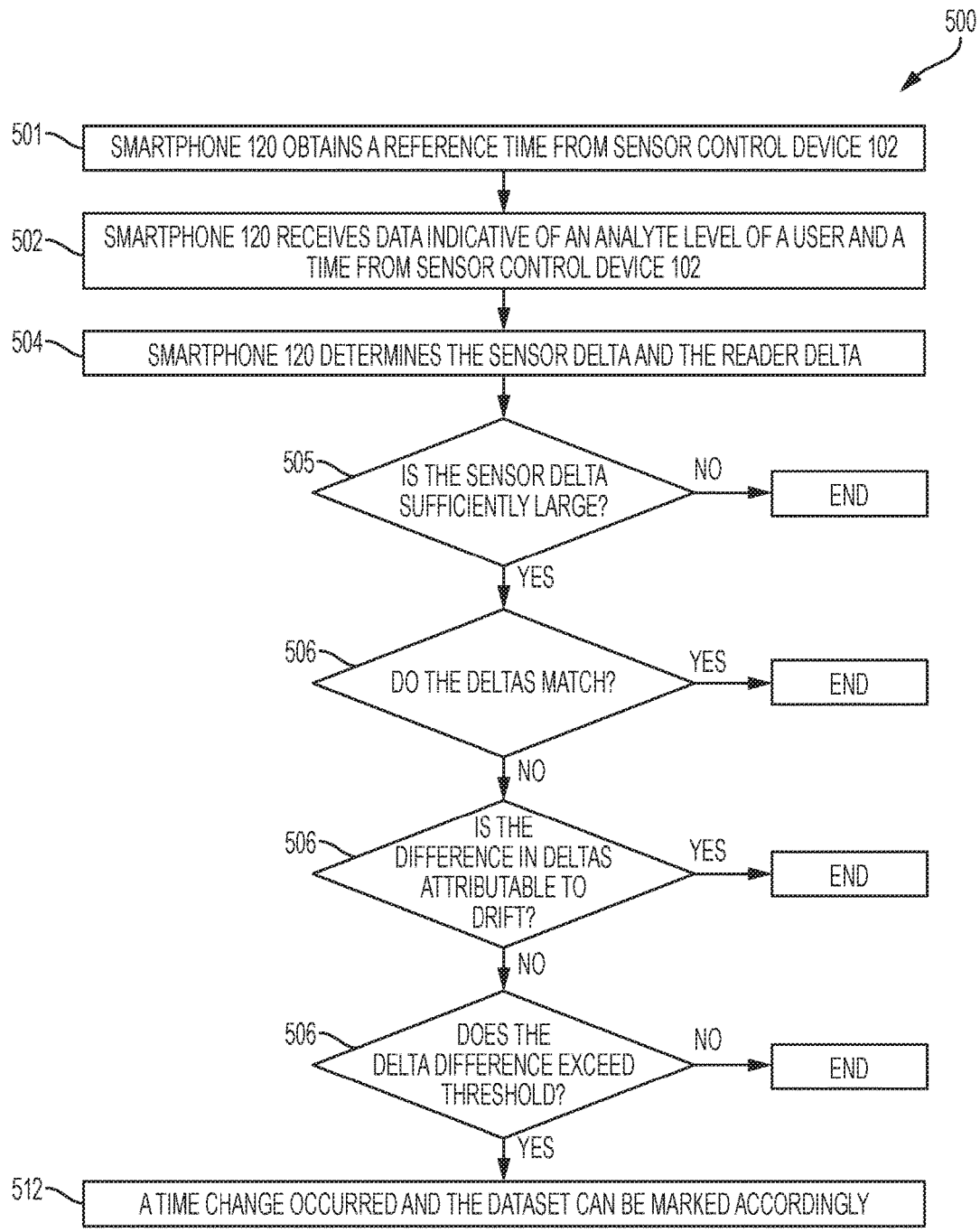
FIG. 5B is a flow chart depicting an example embodiment of a method of determining whether a time change occurred in a reader device.

Embodiments are provided herein that consult multiple clock data sources to reliably and automatically detect significant time change events. FIG. 5B is a flow diagram depicting a method 500 of detecting time changes in the system clock (e.g., see clock 219 of FIG. 6B) of a reader 120, which in this embodiment is a smartphone. At 501, smartphone reader 120 obtains a reference time from sensor control device 102. This can be a timestamp of recently collected analyte data received from sensor control device 102, or a time of activation of sensor control device, or any other time that can be used as a reference point by smartphone reader 120 to correlate the sensor control device's time to the smartphone's time.

At 502, smartphone reader 120 receives data indicative of an analyte level of a user from sensor control device 102 (e.g., as a result of an NFC scan). Smartphone reader 120 also receives a timestamp for the analyte data generated by a clock of sensor control device 102 (e.g., see clock 255 of FIG. 6C) that indicates when the analyte data was sensed or collected. If a scan is performed then the analyte data will be time stamped with a time that is essentially current. But if a significant delay occurs between data collection and transmission, e.g., 5 minutes or more, then sensor control device 102 can send a current time value as well. As noted in the description of FIG. 6C, this timestamp may be an actual time value or may be an integer value reflecting the amount of time that has passed since sensor control device activation (e.g., the number of seconds, or the number of minutes).

At 504, smartphone reader 120 compares the timestamp of the analyte data received (or the current time or other time value) from sensor control device 102 with the reference time obtained from sensor control device 102 in step 501 to determine the difference, i.e., the sensor delta. Smartphone reader 120 also compares the time on the smartphone clock that the analyte data was received (or current time or other time value) with the time on the smartphone clock that correlates to the reference time obtained in step 501 to determine the difference, i.e., the reader delta. At 505, it can be determined whether the sensor delta is sufficiently large to warrant a time change analysis by comparison of the sensor delta to a minimum time change threshold. If the sensor delta is too small, e.g., less than 5 minutes, less than 10 minutes, less than 15 minutes, and so forth, then it may not be worthwhile for the system to perform a time change evaluation. For example, the system may have a minimum threshold that prevents the display of data taken too close together in time. If the sensor delta is sufficiently large, then the process can proceed to 506. Otherwise the process can cease.

At 506, the sensor delta and the reader delta are compared. If no time change has occurred in the time between steps 501 and 502, then the sensor delta and reader delta will be the same and process 500 can end. If the two deltas do not match, then it is possible that a user initiated time change occurred and the process proceeds to 508.

At 508, smartphone reader 120 will analyze whether the change can be attributed to drift or causes other than a change resulting from a user adjusting the clock. For example, a maximum drift can be determined taking into account the error tolerances of the two clocks (e.g., 219 and 255). The clock tolerances will differ by implementation. In some embodiments, the tolerance for the clocks of the sensor control device and the reader device can the same or different, and can be +/−1%, 2%, 3% and so forth, but may be much smaller as well.

If the difference in deltas is less than the maximum drift, then smartphone reader 120 will not attribute the possible time change to user action but rather to drift, and cease the process. If the difference in deltas is greater than the maximum drift, then process 500 can conclude that a time change occurred and proceed to 512. Alternatively, it can be separately determined whether the sensor delta is within the maximum drift for the sensor control device's clock, and whether the reader delta is within the maximum drift for the smartphones clock and, if either or both are outside of the respective maximums conclude that a time change is possible and proceed.

Process 500 can also assess whether the time change is significant enough for the application by comparing the time change to a minimum threshold at 510. The threshold can be, for example, one or two minutes, or any other value that filters out time changes that would be insignificant for the application. Excessive display of time change icons even when little or no risk of overlap will be present can be undesirable.

If the time change is less than the threshold, e.g., only on the order of one or two minutes, then process 500 can cease. If the time change is greater than the threshold, then process 500 can conclude that a time change occurred and, at 512, mark the dataset as having a time change or otherwise cause the display of a time change icon 426 in any analyte graphs (glucose value, rate of change, glucose trends, etc.) and/or cause the display of a similar icon or notation in any log or logbook feature (such as a list, table, or spreadsheet). Marking the dataset may include sending a notification from a sensor interface application responsible for interfacing with sensor control device 102 across an API to a user interface application responsible for generating the displays for the user.

As one of ordinary skill in the art will recognize after reading this disclosure, given the nature of process 500 steps may be performed in various orders (e.g., step 505 can be performed at any time) and some steps may be omitted if not desired for the actual implementation, including but not limited to steps 505, 512, and 514.

Figure 6A:
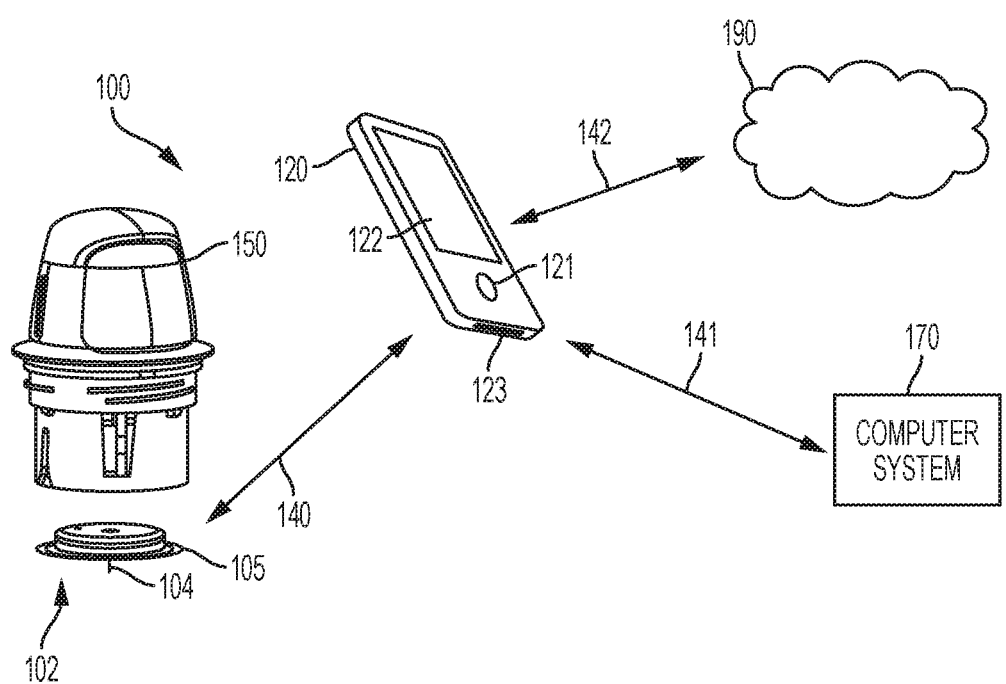
FIG. 6A is a high level diagram depicting an example embodiment of an analyte monitoring system for real time analyte (e.g., glucose) measurement, data acquisition and/or processing.

FIG. 6A is an illustrative view depicting an example embodiment of in vivo analyte monitoring system 100 with which the embodiments described thus far may be used. System 100 is depicted here with a single sensor control device 102 and a single reader device 120, but multiple iterations of each may be present as in the embodiments described above. Sensor control device 102 and reader device 120 can communicate with each other over a local communication path (or link) 140, which can be wired or wireless, and uni-directional or bi-directional. In embodiments where path 140 is wireless, a near field communication (NFC) protocol, RFID protocol, Bluetooth or Bluetooth Low Energy protocol, Wi-Fi protocol, proprietary protocol, or the like can be used. Reader device 120 is also capable of wired, wireless, or combined communication over communication paths (or links) 141 and 142 with other systems or devices, such as a computer system 170 (e.g., a server for a website, a personal computer, a tablet, and the like) or cloud-based storage 190. Communication paths 141 and 14 can be part of a telecommunications network, such as the internet, a Wi-Fi network, a local area network (LAN), a wide area network (WAN), or other data network.

Variants of devices 102 and 120, as well as other components of an in vivo-based analyte monitoring system that are suitable for use with the system, device, and method embodiments set forth herein, are described in US Patent Application Publ. No. 2011/0213225 (the '225 Publication), which is incorporated by reference herein in its entirety for all purposes.

Sensor control device 102 can include a housing 103 containing in vivo analyte monitoring circuitry and a power source (shown in FIG. 2B). The in vivo analyte monitoring circuitry is electrically coupled with an analyte sensor 104 that extends through a patch 105 and projects away from housing 103. An adhesive layer (not shown) can be positioned at the base of patch 105 for attachment to a skin surface of the user's body. Other forms of body attachment to the body may be used, in addition to or instead of adhesive. Sensor 104 is adapted to be at least partially inserted into the body of the user, where it can make contact with the user's bodily fluid and, once activated, used with the in vivo analyte monitoring circuitry to measure and collect analyte-related data of the user. Generally, sensor control device 102 and its components can be applied to the body with a mechanical applicator 150 in one or more steps, as described in the incorporated '225 Publication, or in any other desired manner.

After activation, sensor control device 102 can wirelessly communicate the collected analyte data (such as, for example, data corresponding to monitored analyte level and/or monitored temperature data, and/or stored historical analyte related data) to reader device 120 where, in certain embodiments, it can be algorithmically processed into data representative of the analyte level of the user and then displayed to the user and/or otherwise incorporated into a diabetes monitoring regime.

As shown in FIG. 6A, reader device 120 includes a display 122 to output information to the user and/or to accept an input from the user (e.g., if configured as a touch screen), and one optional user interface component 121 (or more), such as a button, actuator, touch sensitive switch, capacitive switch, pressure sensitive switch, jog wheel or the like. Reader device 120 can also include one or more data communication ports 123 for wired data communication with external devices such as computer system 170 (described below). Reader device 120 may also include an integrated or attachable in vitro meter, including an in vitro test strip port (not shown) to receive an in vitro analyte test strip for performing in vitro blood analyte measurements.

Computer system 170 can be used by the user or a medical professional to display and/or analyze the collected analyte data with an informatics software program. Computer system 170 may be a personal computer, a server terminal, a laptop computer, a tablet, or other suitable data processing device, and can be (or include) software for data management and analysis and communication with the components in analyte monitoring system 100.

The processing of data and the execution of software within system 100 can be performed by one or more processors of reader device 120, computer system 170, and/or sensor control device 102. For example, raw data measured by sensor 104 can be algorithmically processed into a value that represents the analyte level and that is readily suitable for display to the user, and this can occur in sensor control device 102, reader device 120, or computer system 170. This and any other information derived from the raw data can be displayed in any of the manners described above (with respect to display 122) on any display residing on any of sensor control device 102, reader device 120, or computer system 170. The information may be utilized by the user to determine any necessary corrective actions to ensure the analyte level remains within an acceptable and/or clinically safe range.

As discussed above, reader device 120 can be a mobile communication device such as, for example, a Wi-Fi or internet enabled smartphone, tablet, or personal digital assistant (PDA). Examples of smartphones can include, but are not limited to, those phones based on a WINDOWS operating system, ANDROID operating system, IPHONE operating system, PALM WEBOS, BLACKBERRY operating system, or SYMBIAN operating system, with network connectivity for data communication over the internet or a local area network (LAN).

Reader device 120 can also be configured as a mobile smart wearable electronics assembly, such as an optical assembly that is worn over or adjacent to the user's eye (e.g., a smart glass or smart glasses, such as GOOGLE GLASSES). This optical assembly can have a transparent display that displays information about the user's analyte level (as described herein) to the user while at the same time allowing the user to see through the display such that the user's overall vision is minimally obstructed. The optical assembly may be capable of wireless communications similar to a smartphone. Other examples of wearable electronics include devices that are worn around or in the proximity of the user's wrist (e.g., a watch, etc.), neck (e.g., a necklace, etc.), head (e.g., a headband, hat, etc.), chest, or the like.

Figure 6B:
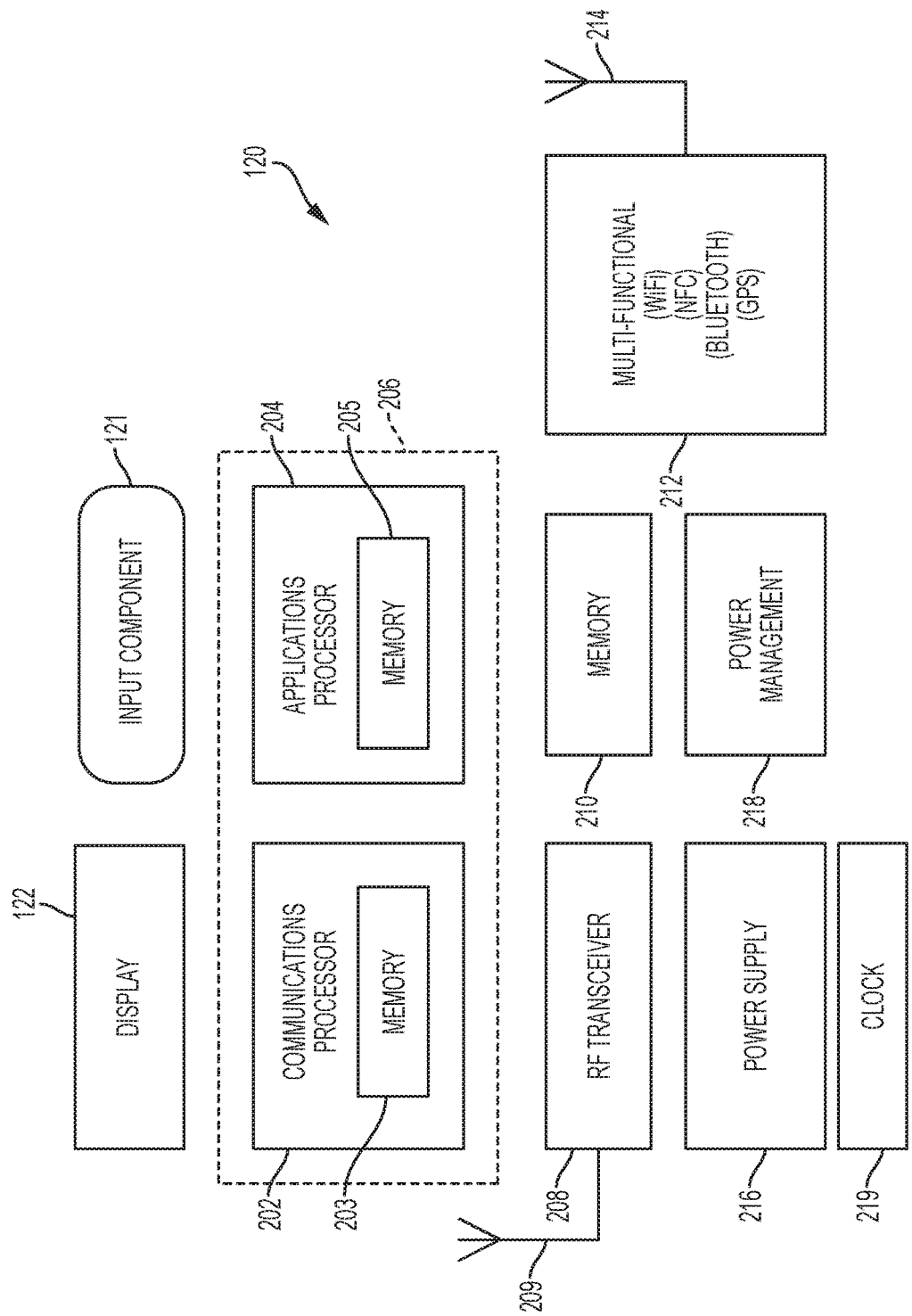
FIG. 6B is a block diagram depicting an example embodiment of a reader device configured as a smartphone.

FIG. 6B is a block diagram of an example embodiment of a reader device 120 in the form of a smartphone. Here, reader device 120 includes an input component 121, display 122, and processing hardware 206, which can include one or more processors, microprocessors, controllers, and/or microcontrollers, each of which can be a discrete chip or distributed amongst (and a portion of) a number of different chips. Processing hardware 206 can include a communications processor 202 having on-board memory 203 and an applications processor 204 having on-board memory 205. Additional processors can and will likely be present. Reader device 120 further includes an RF transceiver 208 coupled with an RF antenna 209, a memory 210, multi-functional circuitry 212 with one or more associated antennas 214, a power supply 216, and power management circuitry 218. FIG. 6B is an abbreviated representation of the internal components of a smartphone, and other hardware and functionality (e.g., codecs, drivers, glue logic, etc.) can of course be included.

Communications processor 202 can interface with RF transceiver 208 and perform analog-to-digital conversions, encoding and decoding, digital signal processing and other functions that facilitate the conversion of voice, video, and data signals into a format (e.g., in-phase and quadrature) suitable for provision to RF transceiver 208, which can then transmit the signals wirelessly. Communications processor 202 can also interface with RF transceiver 208 to perform the reverse functions necessary to receive a wireless transmission and convert it into digital data, voice, and video.

Applications processor 204 can be adapted to execute the operating system and any software applications that reside on reader device 120, process video and graphics, and perform those other functions not related to the processing of communications transmitted and received over RF antenna 209. Any number of applications can be running on reader device 120 at any one time, and will typically include one or more applications that are related to a diabetes monitoring regime, in addition to the other commonly used applications that are unrelated to such a regime, e.g., email, calendar, weather, etc.

Memory 210 can be shared by one or more the various functional units present within reader device 120, or can be distributed amongst two or more of them (e.g., as separate memories present within different chips). Memory 210 can also be a separate chip of its own. Memory 210 is non-transitory, and can be volatile (e.g., RAM, etc.) and/or non-volatile memory (e.g., ROM, flash memory, F-RAM, etc.).

Multi-functional circuitry 212 can be implemented as one or more chips and/or components, including communication circuitry, that perform other functions such as local wireless communications (e.g., Wi-Fi, Bluetooth, Bluetooth Low Energy) and determining the geographic position of reader device 120 (e.g., global positioning system (GPS) hardware). One or more other antennas 214 are associated with both the functional circuitry 212 as needed.

Power supply 216 can include one or more batteries, which can be rechargeable or single-use disposable batteries. Power management circuitry 218 can regulate battery charging and power supply monitoring, boost power, perform DC conversions, and the like. As mentioned, reader device 120 may also include one or more data communication ports such as USB port (or connector) or RS-232 port (or any other wired communication ports) for data communication with a remote terminal 170, or sensor control device 102, to name a few. A network syncing clock 219 is also present that can provide the system time and include, for example, an RC or crystal oscillator and associated clock buffers and distribution circuitry.

Figure 6C:
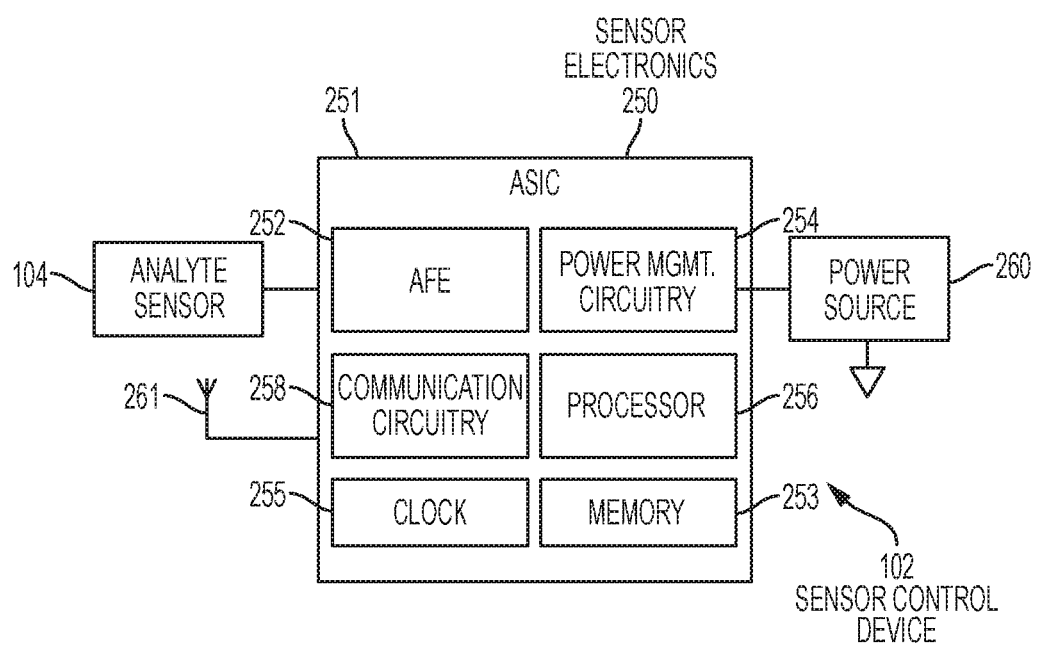
FIG. 6C is a block diagram depicting an example embodiment of a sensor control device.

FIG. 6C is a block schematic diagram depicting an example embodiment of sensor control device 102 having analyte sensor 104 and sensor electronics 250 (including analyte monitoring circuitry). Although any number of chips can be used, here the majority of the sensor electronics 250 are incorporated on a single semiconductor chip 251 that can be, e.g., a custom application specific integrated circuit (ASIC). Shown within ASIC 201 are several high-level functional units, including an analog front end (AFE) 252, power management circuitry 254, processor 256, and communication circuitry 258 (which can be implemented as a transmitter, receiver, transceiver, passive circuit, or otherwise according to the communication protocol). In this embodiment, both AFE 252 and processor 256 are used as analyte monitoring circuitry, but in other embodiments either circuit can perform the analyte monitoring function. Processor 256 can include one or more processors, microprocessors, controllers, and/or microcontrollers.

A non-transitory memory 253 is also included within ASIC 251 and can be shared by the various functional units present within ASIC 251, or can be distributed amongst two or more of them. Memory 253 can be volatile and/or non-volatile memory. In this embodiment, ASIC 251 is coupled with power source 260, which can be a coin cell battery, or the like. AFE 252 interfaces with in vivo analyte sensor 104 and receives measurement data therefrom and outputs the data to processor 256 in digital form, which in turn processes the data to arrive at the end-result analyte discrete and trend values, etc. This data can then be provided to communication circuitry 258 for sending, by way of antenna 261, to reader device 120 (not shown) where further processing can be performed by, e.g., the sensor interface application.

A clock 255 is also present that can be, for example, an RC or crystal oscillator. Clock 255 can be a monotonic clock that moves forward at constant rate (subject to environmental drift) and continues for the entire life of the sensor without interruption. In some embodiments, sensor control device 102 can keep time by generating an interrupt after a predetermined number of seconds (e.g., every second, or every minute etc.), where the interrupt increments a software or hardware counter. The counter value reflects the number of predetermined time spans that have passed since the sensor was activated. For example, if the interrupt is generated every minute, then the counter value reflects the number of minutes that have passed since activation of the sensor control device 102.

It should be noted that the functional components of ASIC 251 can also be distributed amongst two or more discrete semiconductor chips.

Sensor Configurations

Analytes that may be monitored with system 100 include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies, lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times with a single sensor or with a plurality of sensors which may use the same electronics (e.g., simultaneously) or with different electronics of sensor control device 102.

Analyte sensor 104 may include an analyte-responsive enzyme to provide a sensing element. Some analytes, such as oxygen, can be directly electrooxidized or electroreduced on sensor 104, and more specifically at least on a working electrode (not shown) of a sensor 104. Other analytes, such as glucose and lactate, require the presence of at least one electron transfer agent and/or at least one catalyst to facilitate the electrooxidation or electroreduction of the analyte. Catalysts may also be used for those analytes, such as oxygen, that can be directly electrooxidized or electroreduced on the working electrode. For these analytes, each working electrode includes a sensing element proximate to or on a surface of a working electrode. In many embodiments, a sensing element is formed near or on only a small portion of at least a working electrode.

Each sensing element includes one or more components constructed to facilitate the electrochemical oxidation or reduction of the analyte. The sensing element may include, for example, a catalyst to catalyze a reaction of the analyte and produce a response at the working electrode, an electron transfer agent to transfer electrons between the analyte and the working electrode (or other component), or both.

Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes including ferrocene. Examples of inorganic redox species are hexacyanoferrate (III), ruthenium hexamine, etc. Additional examples include those described in U.S. Pat. Nos. 6,736,957, 7,501,053 and 7,754,093, the disclosures of each of which are incorporated herein by reference in their entirety.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

Embodiments of polymeric electron transfer agents may contain a redox species covalently bound in a polymeric composition. An example of this type of mediator is poly (vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation.

Another example of an ionically-bound mediator is a positively charged polymer including quaternized poly (4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, including 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing elements may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, including a glucose oxidase, glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent, which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

In certain embodiments, the sensor works at a low oxidizing potential, e.g., a potential of about +40 mV vs. Ag/AgCl. These sensing elements use, for example, an osmium (Os)-based mediator constructed for low potential operation. Accordingly, in certain embodiments the sensing elements are redox active components that include: (1) osmium-based mediator molecules that include (bidente) ligands, and (2) glucose oxidase enzyme molecules. These two constituents are combined together in the sensing elements of the sensor.

A number of embodiments of sensor configurations that may be used in system 100 are described in Int'l Publication No. WO 2012/174538, titled "Connectors for Making Connections between Analyte Sensors and Other Devices," and also in U.S. Pat. No. 8,435,682, titled "Biological Fuel Cell and Methods," both of which are incorporated by reference herein in their entirety for all purposes. Particular attention is drawn to paragraphs 121-145 of the '528 Publication, several of which are reproduced herein.

The subject matter described herein was done so primarily in the context of in vivo analyte monitoring systems. In vivo systems can be differentiated from "in vitro" systems that contact a biological sample outside of the body (or rather "ex vivo") and that typically include a meter device that has a port for receiving an analyte test strip carrying the biological sample of the user, which can be analyzed to determine the user's blood sugar level. Many in vitro systems require a "finger stick" to obtain the biological sample. In vivo analyte monitoring systems, however, can operate without the need for finger stick calibration.

The embodiments described herein can be used with in vivo analyte monitoring systems that incorporate in vitro capability, as well has purely in vitro or ex vivo analyte monitoring systems. Furthermore, the embodiments described herein can be used in systems, devices, and methods outside of the analyte monitoring field, either in other medical device fields, or in any other field where the subject matter described herein can reap benefit.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description.

As used herein and in the appended claims, the singular forms "a", "an", and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method of pairing devices in an in vivo analyte monitoring environment, the method comprising:
    activating a sensor control device adapted for in vivo analyte sensing, wherein the sensor control device comprises a non-transitory memory that, prior to activation, has a token stored thereon:
    communicating the token to a second reader device;
    sending, by the second reader device, a first communication comprising the token to the sensor control device after the sensor control device has already communicated with a first reader device;
    if the token is valid for the sensor control device, then sending, by the sensor control device, data indicative of a sensed analyte level to the second reader device and displaying the sensed analyte level on a display of the second reader device; and
    if the token is not valid for the sensor control device, then sending, by the sensor control device, a communication to the second reader device that indicates that the token is not valid.

2. The method of claim 1, wherein the second reader device is a smartphone.

3. The method of claim 1, wherein the first communication further comprises a request for data indicative of the analyte level of the user.

4. The method of claim 1, wherein the token is communicated to the second reader device by manually typing the token into the second reader device.

5. The method of claim 4, wherein the token is printed on packaging for the sensor control device.

6. The method of claim 4, wherein the token is displayed by the first reader device.

7. The method of claim 1, wherein the token is communicated to the second reader device automatically.

8. The method of claim 7, wherein the token is in the form of a bar-code and is communicated automatically to the second reader device using an optical scanner of the second reader device.

9. The method of claim 7, wherein the token is communicated wirelessly to the second reader device using a Near Field Communication or Bluetooth protocol.

10. The method of claim 1, further comprising:
activating the sensor control device with the first reader device;
entering the token into the first reader device; and
sending the token from the first reader device to the sensor control device such that the sensor control device can store the token for later use.

11. The method of claim 10, further comprising:
sending, from the first reader device, a request for data indicative of the analyte level of the user to the sensor control device, wherein the request includes the token.

12. The method of claim 11, further comprising:
determining, by the sensor control device, whether the token contained in the request from the first reader device is valid; and
if the token is valid, then sending the data indicative of the analyte level of the user to the first reader device.

13. The method of claim 12, wherein the sensor control device is programmed to respond to a request for data indicative of the analyte level from any one of a plurality of three or more reader devices provided that the reader device that sends the request also communicates the token to the sensor control device, and the sensor control device determines that the token is valid.

14. The method of claim 10, further comprising:
estimating, by the second reader device, either a time at which the sensor control device was activated by the first reader device or a duration of time during which the sensor control device has been active.

15. The method of claim 10, further comprising:
receiving, by the second reader device, a communication from the first reader device comprising either a time at which the sensor control device was activated by the first reader device or a duration of time during which the sensor control device has been active.

16. The method of claim 1, wherein the sensor control device is communicatively paired with the first reader device, and the second reader device is communicatively paired with the sensor control device prior to sending the first communication comprising the token to the sensor control device.

17. The method of claim 1, further comprising:
sending, from the first reader device to the sensor control device, a first identifier that is unique to the first reader device; and
sending, from the second reader device to the sensor control device, a second identifier that is unique to the second reader device.

18. The method of claim 17, further comprising:
communicating analyte data, from the sensor control device to the first reader device, if the first identifier that is unique to the first reader device is on an approved list.

19. The method of claim 1, wherein communicating the token to the second reader device comprises sending the token from the first reader device to the second reader device over a Bluetooth or Bluetooth Low Energy wireless link.

20. The method of claim 1, wherein the first reader device is a dedicated-use reader device and the second reader device is a smartphone.

\* \* \* \* \*